United States Patent
Grass et al.

(10) Patent No.: US 10,577,654 B2
(45) Date of Patent: Mar. 3, 2020

(54) PARTICULATE DISTRIBUTED SENSING ELEMENTS

(71) Applicant: ETH ZURICH, Zurich (CH)

(72) Inventors: Robert N. Grass, Zurich (CH);
Wendelin Jan Stark, Langenthal (CH);
Gediminas Mikutis, Zurich (CH);
Michela Puddu, Zurich (CH)

(73) Assignee: ETH Zurich, Zurich (CH)

(*) Notice: Subject to any disclaimer, the term of this patent is extended or adjusted under 35 U.S.C. 154(b) by 251 days.

(21) Appl. No.: 15/567,989

(22) PCT Filed: Apr. 19, 2016

(86) PCT No.: PCT/EP2016/058600
§ 371 (c)(1),
(2) Date: Oct. 20, 2017

(87) PCT Pub. No.: WO2016/169904
PCT Pub. Date: Oct. 27, 2016

(65) Prior Publication Data
US 2018/0119220 A1    May 3, 2018

(30) Foreign Application Priority Data
Apr. 20, 2015 (EP) .................... 15164214

(51) Int. Cl.
*C12Q 1/6876* (2018.01)
*C12Q 1/68* (2018.01)
*B01L 3/00* (2006.01)

(52) U.S. Cl.
CPC .............. *C12Q 1/6876* (2013.01); *B01L 3/54* (2013.01); *C12Q 1/68* (2013.01); *B01L 2400/043* (2013.01)

(58) Field of Classification Search
None
See application file for complete search history.

(56) References Cited

U.S. PATENT DOCUMENTS

| 9,675,953 B2 * | 6/2017 | Oldenburg ............. C01B 33/18 |
| 2009/0253901 A1 * | 10/2009 | Grinberg ............. A61K 9/0019 536/23.1 |
| 2012/0283379 A1 * | 11/2012 | Auger .................. A61K 9/1075 524/556 |

FOREIGN PATENT DOCUMENTS

| GB | 2528716 A * | 2/2016 | ............... C09K 8/03 |
| WO | 2013/054126 A2 | 4/2013 | |
| WO | 2013/143014 A1 | 10/2013 | |

(Continued)

OTHER PUBLICATIONS

Puddu et al. Magnetically recoverable, thermostable, hydrophobic DNA/silica encapsulates and their application as invisible oil tags. ACS Nano 8(3):2677-2685. (Year: 2014).*

(Continued)

*Primary Examiner* — Samuel C Woolwine
(74) *Attorney, Agent, or Firm* — Renner, Otto, Boisselle & Sklar, LLP (57) ABSTRACT

The present invention relates to core-shell particles comprising encapsulated nucleic acids—a sensing sequence and a control sequence; the invention further relates to the use of such particles as a sensing element; to methods for measuring a property of interest in a setting employing such particles; to measuring systems and analytical kits comprising such particles.

21 Claims, 2 Drawing Sheets
Specification includes a Sequence Listing.

(56) References Cited

FOREIGN PATENT DOCUMENTS

WO 2014/143004 A1 9/2014

OTHER PUBLICATIONS

Grass et al. Robust chemical preservation of digital information on DNA in silica with error-correcting codes. Angew. Chem. Int. Ed. 54:2552-2555. (Year: 2015).*

Puddu et al. Submicrometer-sized thermometer particles exploiting selective nucleic acid stability. Small 12(4):452-256. (Year: 2016).*

International Search Report for corresponding International Application No. PCT/EP2016/058600 dated Jul. 7, 2016.

Written Opinion of the International Searching Authority for corresponding International Application No. PCT/EP2016/058600 dated Jul. 7, 2016.

Alaskar et al., "Temperature nanotracers for fractured reservoirs characterization", Journal of Petroleum Science and Engineering, vol. 127, 2015, pp. 212-238.

Anonymous, invitrogen in life technologies, "1 Kb Plus DNA Ladder", 2013, pp. 102, retrieved from the Internet: https://tools.thermofisher.com/content/sfs/manuals/1Kb_Plus_DNA_ladder man.pdf.

Hoop et al., "PCR quantification of SiO2 particle uptake in cells in the ppb and ppm range via silica encapsulated DNA barcodes", Chemical Communications, vol. 50, No. 73, 2014, pp. 10707-10709.

Grass et al., "Tracking Trace Amounts of Submicrometer Silica Particles in Wastewaters and Activated Sludge Using Silica-Encapsulated DNA Barcodes", Environmental Science & Technology Letters, vol. 1, No. 12, 2014, pp. 484-489.

Paunescu et al., "Reversible DNA encapsulation in silica to produce R0S-resistant and heat-resistant snythetic DNA fossils", Nature Protocols, vol. 8, No. 12, 2013, pp. 2440-2448.

Nielsen et al., "Aptamers Embedded in Polyacrylamide Nanoparticles: A tool for in Vivo Metabolite Sensing", ACS NANO, vol. 4, No. 8, 2010, pp. 4361-4370.

Chatterjee et al., "Core/shell nanoparticles in biomedical applications", Advances in Colloid and Interface Science, vol. 209, 2014, pp. 8-3.

Paunescu et al., "Protection and Deprotection of DNA—High-Temperature Stability of Nucleic Acid Barcoes for Polymer Labeling", Angewandte Chemie, vol. 52, 2013, pp. 4269-4272.

* cited by examiner

PARTICULATE DISTRIBUTED SENSING ELEMENTS

This application is a national phase of International Application No. PCT/EP2016/058600 filed Apr. 19, 2016 and published in the English language, and claims priority to European Application No. 15164214.7 filed on Apr. 20, 2015.

The present invention relates to core-shell particles comprising encapsulated nucleic acids, to the use of such particles as a sensing element; to methods for measuring a property of interest in a setting employing such particles, to measuring systems and analytical kits comprising such particles.

The use of nucleic acids as a part of a sensing element is known and described e.g. in Alaskar et al (J. of Petroleum Science and Engineering 2015, 212). The document describes inter alia temperature-sensitive nanotracers for fractured reservoirs characterization. The nanotracers disclosed therein comprise silica-protected DNA particles. It is considered disadvantageous that only one specific property of interest (temperature) can be determined and it is particularly disadvantageous that the set-up provides results with very limited accuracy. This limited accuracy is believed to be due to both (i) incomplete recovery and (ii) non-specific damage to particles and DNA.

Further, encapsulation of nucleic acids is known and described e.g. in Paunescu (Angew. Chem. Int Ed. 2013, 52, 4269-4272). This document discusses high temperature stability of nucleic acid barcodes for polymer labelling). Grass (WO2013/0143014) describes specific core-shell particles suitable for secure marking. These documents, however, do not address the use of such particles for measuring a property of interest in a given setting, nor do these documents contemplate a core having sensing and control sequence as discussed herein. Further, the particles of ex. 16, disclosed in that document, cannot be amplified using PCR, making these particles unsuitable for the uses disclosed in the present invention.

In consequence, there is a need for sensing elements overcoming the drawbacks of the prior art, particularly with improved accuracy and/or broader applicability.

Thus, it is an object of the present invention to mitigate at least some of these drawbacks of the state of the art. In particular, it is an aim of the present invention to provide improved particles capable for sensing a property of interest, methods for detecting a property of interest and devices capable in performing such methods.

These objectives are achieved by the use of particles as defined in claim 1, the particles as defined in claim 2, the method as defined in claim 10 and the measuring system as defined in claim 15. Further aspects of the invention are disclosed in the specification and independent claims, preferred embodiments are disclosed in the specification and the dependent claims. Accordingly, the present invention provides
  in the first aspect for novel core-shell particles
  in the second aspect to the use of core-shell particles as sensing element,
  in the third aspect for methods of measuring a property of interest employing such particles, and
  in the fourth aspect to measuring systems comprising such particles as sensing element.

The present invention will be described in more detail below referring to these aspects.

It is understood that the various embodiments, preferences and ranges as provided/disclosed in this specification may be combined at will. Further, depending of the specific embodiment, selected definitions, embodiments or ranges may not apply.

Unless otherwise stated, the following definitions shall apply in this specification:

As used herein, the term "a", "an" "the" and similar terms used in the context of the present invention (especially in the context of the claims) are to be construed to cover both the singular and plural unless otherwise indicated herein or clearly contradicted by the context. Further, the term "containing" shall include both, "comprising" and "consisting of".

The term "encapsulation of nucleic acids" is known in the field and describes a procedure where nucleic acids are enclosed in a protective environment ("shell", "cage"). By encapsulation unwanted side reactions are decreased. In line with the present invention, encapsulated nucleic acids are still accessible to a property of interest. Examples of encapsulation are inclusion in silica, bone-like materials, and polymer capsules. The term encapsulation is to be distinguished from "caging nucleic acids", the latter term being used to describe a specific modification of nucleic acids, which makes them inactive.

The term "particle" is known in the field and includes "microparticles" and "nanoparticles". Nanoparticles are solid spheres with a primary diameter between 10 and 100 nm, while microparticles are solid spheres with a primary diameter between 100 and 10000 nm. Nanoparticles and microparticles tend to agglomerate, resulting in larger agglomerates. Such larger agglomerates are still considered "nano-/microparticles". Particles may have various shapes but possess a closed surface, contrary to the open surface of nanotubes. The term "shell" defines an outer layer, completely surrounding a particle's interior region; this interior region is termed "core".

The term "silica" is known in the field and describes the chemical compound $SiO_2$ in its amorphous state. The term "silica'" also includes amorphous glass matrices. Suitable glass matrices have a $SiO_2$ content of at least 50 wt %. Glass matrices consequently may include other elements {particularly selected from the group consisting of carbon, sodium, calcium, cadmium, boron, lead, phosphorous, titanium, zinc, cerium, iron, cobalt, and aluminum).

The term "Nucleic Acid" is known in the field and includes DNA, RNA, and PNA, each described by its nucleic acid sequence. Nucleic acids include both, naturally occurring nucleic acids and artificial nucleic acids ("analogues"). The term also includes nucleic acids that are chemically modified (e.g. carrying protecting groups). The term "Control sequence" describes a nucleic acid that acts as a reference when a property of interest is quantified. It accounts for the natural environmental damage, but is more stable towards the specific property of interest to be quantified than the sensing sequence or is not affected by the property of interested to be quantified at all. The term "Sensing sequence" describes a nucleic acid that is more specifically susceptible to a specific stress of interest than the control sequence, but its response to other conditions is comparable to the one of the control sequence.

In the context of this invention, the term "property of interest" broadly defines any property of a setting to be determined and thus includes chemical properties and physical properties of a given setting. Accordingly, it describes a physical quantity or a chemical entity that is desired to be determined. A specific property of interest affects the sensing sequence significantly more than the control sequence.

The present invention will be better understood by reference to the figures.

FIG. 1 shows a general scheme of measuring method according to the present invention. In step (a), two distinct nucleic sequences (control sequence (1) and sensing sequence (2)) are encapsulated in order to protect them from unspecific damage or in order to make them differently susceptible to a specific property of interest. The thus obtained particles (4), comprising a core of encapsulated nucleic acids and a shell (3) are subjected to stress in a setting (say temperature in a fluid); thereby partly degrading the sensing sequence (b). Following that, the particles are recollected from said setting (c) and stress is quantified by releasing the nucleic acids, determination of the extent of degradation of the two sequences and correlating the data with an established calibration (d).

FIG. 2 shows various embodiments of the inventive particles (4), leading to specific nucleic acid damage according to the invention and thereby forming the basis for measuring a signal. A) Direct interaction of a physical property of interest with the sensing nucleic acid, which induces specific damage on the sensing sequence but not on the control sequence, which is quantified by PCR. B) Interaction of a physical property of interest with a signaling molecule (5), which in turn produces nucleic acid-damaging species (6). This approach is suitable where a specific damage cannot be induced directly on a sensing sequence. C) Direct interaction of a chemical property of interest with a sensing sequence, enabled by analyte diffusing through a porous outer shell (3-2) of the inventive particles and thereby degrading the sensing sequence. The control sequence is located in a robust inner shell (3-1). Degradation of the sensing sequence when compared to the control sequence, is quantified by PCR. D) The chemical or physical property of interest changes the surrounding environment, which results in the degradation of the particle outer shell (3-3) and specific nucleic acid loss, which is quantified. The control sequence is again located in a robust inner shell (3-1). In embodiment A, the control sequence is more resistant to the property of interest than the sensing sequence. In embodiments B-D, the control sequence is encapsulated within a shell which is resistant to the property of interest.

In a first aspect, the invention relates to novel core-shell particles, whereby the particles have a primary particle size of 10-10000 nm, the core comprises a first and a second group of nucleic acids, the shell comprises an inorganic material or an organic material, characterized in that (i) said first group of nucleic acids is adapted to degrade upon exposure to a property of interest ("sensing sequence") and (ii) said second group of nucleic acids is adapted to degrade less upon exposure to this property of interest ("control sequence"). This aspect of the invention shall be explained in further detail below, with particular reference to the structure of the particle, the nature of sensing and control sequence and the nature of the shell:

The term "particle" is defined above; encapsulation of nucleic acids is known and described e.g. in the literature cited above. Particles suitable for the methods and uses described herein comprise two different nucleic acid groups, one nucleic acid group comprising a control sequence, the other nucleic acid group comprising the sensing sequence. The sensor functions by exposing the sensing nucleic acid to the property of interest in a setting, and detecting the resulting damage to the nucleic acid. The relative concentration of the sensing nucleic acid is then compared to the control sequence, and the damage difference is quantified. A general scheme of the experiment is given in figures and further outlined in the following aspects of the invention.

Figure 1:
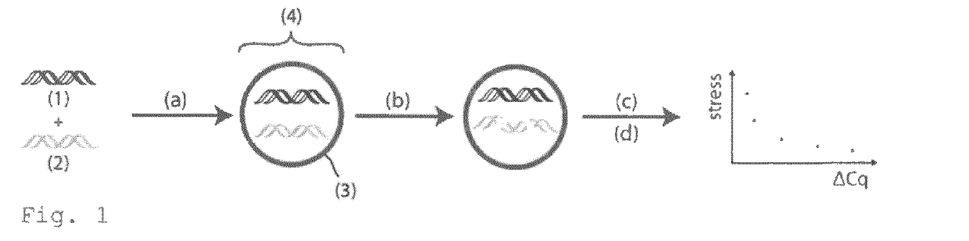
Figure 2:
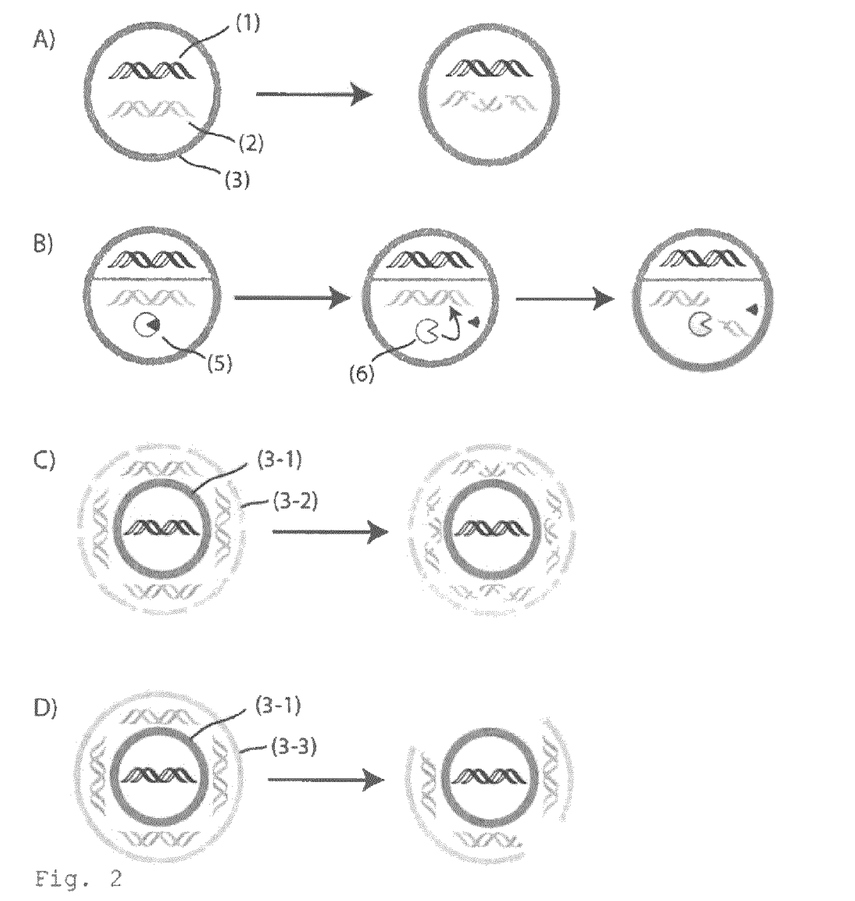
Figure 3:
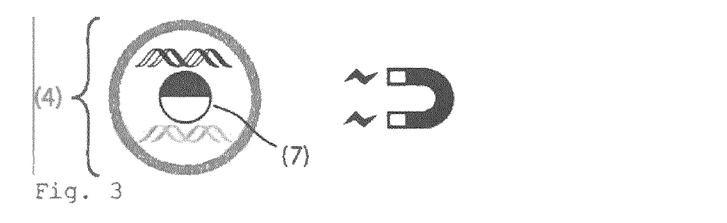
FIG. 3 shows a further embodiment of inventive particles (4). In this embodiment, magnetic particles are additionally located in the particle's core. Such particles are simple to collect from a given setting and thus increase quality of the measurement. This fig. shows as an exemplary embodiment particles according to FIG. 2A, containing additional magnetic particles. It is apparent that also particles according to FIGS. 2B, 2C and 2D may contain such additional magnetic particles.

The inventive core-shell particles may differ in their structure, as schematically shown in FIG. 2 and FIG. 3. Appropriate types of core-shell particles may be chosen depending on the property of interest, the measuring system used and further considerations.

In one embodiment, the invention provides for core-shell particles as described herein, characterized in that said sensing and control sequence are located within one single core. This embodiment is shown in FIG. 2A and also exemplified in example 2 below.

In a further embodiment, the invention provides for core-shell particles as described herein, characterized in that said sensing and control sequences are located in separate cores and a signalling molecule is located in the same core as the sensing molecule. This embodiment is shown in FIG. 2B and also exemplified in example 5 below. The term "signalling molecule" is known in the field and specifically defines any chemical entity that damages or modifies nucleic acids in the close proximity upon specific change in the value of property of interest.

In a further embodiment, the invention provides for core-shell particles as described herein, characterized in that said control sequence is located in an inner core, surrounded by a shell inert towards the property of interest and said sensing sequence is located in an outer core, surrounded by a shell permeable/susceptive towards the property of interest. This embodiment is shown in FIG. 2C and also exemplified in example 6 below.

In a further embodiment, the invention provides for core-shell particles as described herein, characterized in that said control sequence is located in an inner core, surrounded by a shell inert towards the property of interest and said sensing sequence is located in an outer core, surrounded by a shell degrading upon exposure of the property of interest. This embodiment is shown in FIG. 2D.

The term "degradation" of a nucleic acid sequence refers to the relative concentration of nucleic acid lost during exposure to a property of interest. The relative concentration of nucleic acid left in mathematical terms can be defined as $c_{final}/c_0$, and the relative concentration lost as the difference between 1 and relative concentration left $(1-c_{final}/c_0)$, where $c_{final}$ is the concentration after said exposure and $c_0$ is the concentration before said exposure. Thus, the smaller the relative concentration left, the higher the degradation. Degradation can thus be conveniently evaluated by comparing the relative concentration left. Sequence dependent concentrations can be measured by known nucleic acid amplification methods, such as PCR, qPCR, LAMP, SDA, HDA. The quantitative threshold cycle value Cq is defined as an amplification cycle when the amplification curve intersects a threshold line defined by the amplification methods defined above, and is a logarithmic measure of the specific nucleic acid sequence content in a sample. The difference in Cq between after and prior to exposure to the property of interest is defined as $\Delta Cq$ ($\Delta Cq = Cq_{final} - Cq_0$), and can be related to the concentrations with the following equation: $\Delta Cq = \log_2(c_0/c_{final})$. Thus, $\Delta Cq$ indirectly describes the relative concentration lost (the higher the $\Delta Cq$, the higher the degradation). The readout is performed by evaluating the difference in degradation of the nucleic acids ($\Delta\Delta Cq = \Delta Cq$ (control sequence) $- \Delta Cq$ (sensing sequence)) and comparing it to the reference scale established experimentally.

The terms "sensing sequence" and "control sequence" are defined above. Suitable sequences include DNA molecules and RNA molecules. The number of nucleotides in these sequences may vary over a broad range, suitable sequence length is in the range of 50-5000 nucleotides, preferably 50-200 nucleotides. The invention, however, also contemplates the use of longer nucleic acid molecules.

In one embodiment, suitable sequences are selected from the group consisting of naturally occurring sequences. Examples thereof include DNA and RNA extracts from plants, animals, bacteria and viruses.

In one further embodiment, suitable sequences are selected from the group consisting of synthetic sequences. Examples thereof include randomly generated sequences and sequences designed to have specifically higher or lower stability for a given property of interest (DNA vs RNA for temperature or electromagnetic radiation measurement; significantly different % GC content for temperature measurement). Further examples of synthetic sequences include caged sequences. Such sequences are not active in polymerase chain reaction. Upon exposure to a property of interest (usually light, but can also be another property of interest), the sequence is partially uncaged and can be detected using amplification techniques. Examples of caged sequences include 6-nitropiperonyloxymethyl-, 1-(o-nitrophenyl)-ethyl- courmarin- and bromocoumarin-caged oligonucleotides.

As outlined above, the sensing and the control sequence of the inventive particles differ. The sensing sequence is adapted to degrade upon exposure to the property of interest while the control sequence is adapted to not degrade upon exposure to this property of interest. It is apparent that best measurement signals are obtained providing completely stable control sequences.

Accordingly, in an advantageous embodiment, the control sequence is thus selected to not degrade or to essentially not degrade upon exposure to the property of interest. Correspondingly, it is advantageous to select sensing sequences that degrade significantly upon exposure to the property of interest.

However, it was found that suitable measuring signals may also be generated when the control sequence is adapted to degrade significantly less upon exposure to the property of interest, when compared to the sensing sequence. A significantly lower degradation depends on the aimed measuring accuracy and the measuring set up. Suitable sequences and their degradation properties are specifically disclosed in the examples. The following parameters were found to be suitable when exposed to the property of interest:

the relative concentration ($c_{final}/c_0$) of the sensing sequence left after the said exposure is at least 15% ($\Delta\Delta Cq = -0.23$ cycles) lower than that of the control sequence; or preferably the relative concentration ($c_{final}/c_0$) of the sensing sequence left after the said exposure is at least 50% ($\Delta\Delta Cq = 1$ cycle) lower than that of the control sequence; or preferably the relative concentration ($c_{final}/c_0$) of the sensing sequence left after the said exposure is at least 75% ($\Delta\Delta Cq = 2$ cycles) lower than that of the control sequence.

The person skilled in the art is in a position to identify suitable pairs of sensing/control sequence, adapted to the specific need of a particular property of interest and to the need of a specific setting. Typically, said sensing and control sequence differ by five or more nucleotides.

The different behaviour of sensing and control sequences when exposed to the property of interest is believed to be one key feature of the present invention. By this feature, a measuring method as outlined below (the $3^{rd}$ aspect of the invention) now differentiates between the measurement signal originating from the property of interest (such as nucleic acid loss upon thermal degradation) and measurement signals originating from other factors (such as nucleic acid loss due to tracer dilution, nucleic acid loss due to non-thermal nucleic acid degradation). This provides for a significantly improved measuring accuracy over methods known until now. This finding is supported by the experiments provided below, particularly #2.2, and #3.3, outlining the relevance of both sequences to be present: sensing sequence and control sequence.

The term "shell" is defined above. In line with the present invention, a wide range of materials may be used.

In one embodiment, the shell contains, particularly consists of, silica. This embodiment allows simple manufacturing of the particles and also provides particles being chemically inert.

In one further embodiment, the shell contains silica and an additional inorganic coating. Such inorganic coating may be selected from the group of metal oxides and metal sulfides, such as titanium oxide, zinc sulfide, cerium oxide, cadmium sulfide. This embodiment is advantageously applied to further protect the nucleic acids from external damage.

In one further embodiment, the shell contains silica and an additional inorganic coating selected from the group of metals, such as gold, and silver. This embodiment is advantageously applied to further protect the nucleic acids from external damage.

In one further embodiment, the shell contains silica with surface functionalization by organic molecules, such as PEGs, alkylsilanes (e.g dodecylsilane). This embodiment is advantageously applied to change the surface properties (e.g. polarity or dispersion) of the sensing element.

In one further embodiment, the shell contains a polymeric coating. Suitable polymers may be selected from the group of polyethylene, poly-propylene, polyvinyl chloride, poly-epoxide, poly-tetrafluoroethylene, aramide, polyester (such as SU8), polyurethane, polylactic acid, poly-3-hydroxybutyrate, polyethylene terephthalate, polybutylene terephthalate, polystyrene, polycarbonate, polyamide, polyacrylate, poly(methyl methacrylate), polysulfone, polyoxymethylene, polyethersulfone, polyphenylsulfone, polyether ether ketone (PEEK), basic methacrylate copolymer (BMC), Poly (butyl methacrylate-co-(2-dimethylaminoethyl) methacrylate-co-methylmethacrylate), Eudragit®), poly-benzimidazole, ethylene chlorotrifluoro-ethylene, poly-dimethylsiloxane, polyamide-imide, poly(p-phenylene sulfide), polyvinylidene difluoride, Polydiallyldimethylammonium chloride, poly-(vinyl-pyrrolidone), poly(acrylic acid), poly-(methacrylic acid) (also thiolated derivative), poly-(2-ethylacrylic acid), poly-(2-propylacrylic acid), poly-(dimethylaminoethyl methacrylate), poly-(diethylaminoethyl methacrylate), poly-(N-ethylpyrrolidine)-methacrylate, poly-(N-isopropyl-acrylamide) and combinations thereof. These polymer coatings are selected to result in (partial) degradation upon change in pH, temperature, reduction potential, or specific chemical composition in the environment (e.g. acetal/ketal linkages; disulfides, esters), and may be chosen by the skilled person according to the specific need. This embodiment is advantageously applied in case of permeable or degrading outer shells. This embodiment is shown in FIGS. 2C and 2D and also exemplified in example 6 below. In this embodiment, the outer shell may be selected to be permeable to small-molecules of interest (such as radical species); or sensitive to mild changes in environment (such as pH, humidity, reduction potential).

In one further embodiment, the particles further comprise magnetic material. Said magnetic material may be present in the core in the form of small particles. Advantageously, such materials have soft magnetic properties and include iron oxides, mixed oxides containing iron and the metals cobalt, nickel and iron as well as alloys and metal carbides thereof. The content of such soft magnetic material is chosen to obtain particles with a saturation magnetization of at least 5 emu/g and having soft magnetic properties, defined by a coercivity of less than 50 Oersted. By the presence of magnetic material, the measuring accuracy and sensitivity may be improved. This is outlined below in the third aspect of the invention, step (c).

In more general terms, in a second aspect, the invention relates to the use of core-shell particles (4) as defined herein as a sensing element. According to this aspect of the invention, the core-shell particles act as distributed sensors and are capable of measuring a property of interest. This aspect of the invention shall be explained in more detail below:

Property of interest: This term is described above and refers to a property of a setting to be determined and thus includes chemical properties and physical properties of a given setting. By exposing the core-shell particles to the property of interest, physical or chemical stress is applied. By exposing to this stress, the structural changes of the encapsulated nucleic acid is observed (typically a partial degradation) which is the characterizing property of the sensing element to be detected.

Physical properties include temperature, exposure to electromagnetic radiation, and exposure to radioactive radiation.

Chemical properties include pH, oxidative stress, humidity, reduction potential, genotoxicity, chemical reactivity, metal ion content, microbial activity, and metabolic activity. The term "oxidative stress" is known in the field and particularly refers to chemically reactive entities. The term includes stress induced by a "reactive oxygen species (ROS)" carrying an oxygen atom, and "reactive nitrogen species (RNS)". The term "microbial activity" is known in the field and particularly refers to the presence and viability of microorganisms and their chemical turnover (e.g. as can be expressed by an MTT assay). The term "metabolic activity" is known in the field and particularly refers to the chemical turnover of a living system, (e.g. the rate of ATP turnover).

Distributed sensor: Distributed sensors are sensors, which can be dispersed within a medium and are recollected for readout (see the third aspect of the invention). Following distribution and recollection, such distributed sensors then either carry the time history of a sensor signal, or a cumulated sensor signal. Utilizing suitable analytical technology, the sensor signal can be collected from the individual sensors and can be utilized to give a localized sensor result. Distributed sensors also allow sensing at settings, which are difficult to access (e.g. too small, harsh conditions) to accommodate conventional sensors. A distributed sensor is placed in the sensing location, herein referred to as "setting" (700), for a given duration, recollected and the sensor signals are read out from the sensor.

In a third aspect, the invention relates to a method of measuring a property of interest (a "stress") in a setting (700), said method comprising the step of contacting core-shell particles (4) as defined herein with said setting (700) and the step of determining structural differences of said particle core. This aspect of the invention shall be explained in further detail below:

The term "property of interest", or simply "stress", is discussed above and includes chemical and physical stress.

The term "setting" defines any environment where a stress is to be determined. Such settings include liquid and solid matrices. Specific settings include:
  matrices of biological origin;
  settings in mining, energy and water supply and recycling industries;
  environmental settings;
  Polymers.

Matrices of biological origin include cells, living organisms, blood and other body fluids. Matrices of biological origin thus include settings in vivo, ex vivo and in vitro. Living organisms include unicellular organisms (such as bacteria, archaea, protozoa, unicellular algae and unicellular fungi) and multicellular organisms (such as algae, plants, animals (including mammals such as humans)).

Settings in mining, energy and water supply and recycling industries include reservoirs, piping systems, sewage disposal systems and their characterization.

Environmental settings include rivers (including basins), lakes, soil samples and the like.

Polymers include technical and consumer products made of plastics.

In one embodiment, the method comprises the steps of (a) providing core-shell particles (4) as defined herein; (b) distributing said particles in said setting (700) thereby exposing them to the property of interest; (c) collecting said particles; and (d) analysing said particles. These individual steps are known per se, but not yet applied in the context of the particles described herein.

Step (a): Advantageously, step (a) comprises preparing a dispersion of core-shell particles as defined herein in a liquid. Such liquid may be aqueous or non-aqueous.

The viscosity of said liquid may vary; low-viscosity liquids are preferred, i.e. having a viscosity below 100 mPa·s.

It is apparent from the above that the core-shell particles must be selected in view of the property of interest to be detected. The method described herein requires a damage of nucleic acids in the core-shell particles when exposed to a stress in a setting. Specific damage to nucleic acids can be detected using one of the three setups:

(a1) by direct interaction of the property of interest with nucleic acids, which induces specific damage that is quantified by PCR (FIGS. 2A and 2C);
(a2) by inducing stress on signaling molecules, which in turn produce nucleic acid-damaging species. This approach is needed when the specific damage cannot be induced directly on the nucleic acid itself (FIG. 2B);
(a3) by changing the surrounding environment, which results in the degradation of the particle protective coating and specific nucleic acid loss, which is quantified (FIG. 2D).

Step (b): Advantageously, said step (b) comprises mixing the dispersion with the medium in which the property is to be measured. Such mixing may be done passively, e.g. by flow in the setting. Alternatively, such mixing may be done actively, e.g mechanical mixing, shaking, or ultrasound mixing.

Due to step (b) distribution of particles in a setting, the method described herein may be termed "Distributed sensing" and shows a number of benefits:

The inventive method is very versatile and allows for dispersed sensing a wide range of physical properties (e.g. temperature, light, humidity) and a wide range of chemical properties (ROS, metal ion content, etc.).

The inventive method allows for distributed sensing of a property of interest in complex settings, such as online reactors or ecosystems, particularly where taking a measure in one spot is insufficient. It also allows measuring in settings that are difficult to access, e.g. due to their size (e.g. microorganisms), due to harsh conditions (e.g. geological resources), due to compatibility (e.g. in vivo).

The inventive method allows for long-term sensing/quality control. This is an important feature, as control of a complete population with current technology is often impossible or too expensive. For example, blood quality control cannot be performed at an affordable price on every sample after every step of preparation, packing, transport, recovery, and further use.

Step (c): Advantageously, said step (c) comprises the collection of said particles by (c1) applying a magnetic field and/or (c2) centrifugation. Removing of particles from the setting may be a challenging task. In previously applied methods (discussed above), this task was a major source of improper/inaccurate measuring. By providing the inventive particles comprising a sensing and a control sequence, it is no longer important to recollect all or a specified fraction of particles after measuring took place. The control sequence is an internal reference against which the signal is taken. Centrifugation was found suitable for collecting a sufficient amount of particles for the following step. When using magnetic particles, it is particularly simple collecting the particles. This may be achieved simply by placing a magnet to the setting and to thereby collect the particles.

Step (d): Detection of nucleic acids may be performed in any known manner. Advantageously, step (d) comprises (d1) liberating said nucleic acids from said particle e.g. by use of a fluoride ion containing aqueous solution and (d2) purifying the nucleic acids by commercially available nucleic acid purifying technique and (d3) subjecting the thus obtained nucleic acid solution to an amplification reaction and (d4) detecting the concentration of two or more nucleic acid sequences.

Step d1: This step is known per se. In case of a silica shell (pure, coated, modified), agents capable of dissolving silica may be selected by the skilled person. Fluoride containing buffers may be used.

Suitable are, for example, solutions with a pH of 3-7 that contain fluoride ions in a concentration of 0.0001-10 wt-%, preferably 0.01-10 wt-%.

In case of a polymer shell, agents capable of dissolving such polymers may be selected by the skilled person.

The method of measuring a property of interest as discussed herein is very powerful. Even if 99.9999% of the core-shell particles are lost during the measuring, ie. the ratio of particles obtained in step (c)/particles provided in step (a) is 1/1.000.000=1 ppm, a measuring signal can be obtained. This is a significant improvement over the prior art and further outlined in the examples. Particularly, examples 2.2 and 3.3 demonstrate that only fractional recovery of the sensing elements is sufficient to determine a property of interest (temperature in this case). When compared to the prior art (Alaskar et al.), examples prove that the current development allows a precise readout of temperature from a small fraction of recovered particles (which is the case in any open setting). The proposal of Alaskar et al would require recovering a complete set of particles from an underground setup, which is not realistic.

Furthermore, example 3.1 shows that the presented particles containing two sequences that degrade to a different extent and can be measured independently, allow measuring temperature based on the difference in the relative amounts of nucleic acids detected. When compared with prior art (Grass et al.), the current embodiment allows determining the concentration of each of the nucleic acids, and relate it to the cumulative temperature. The prior art merely presents particles with more than one distinct nucleic acid, but only one of them could be amplified, and the temperature in such setup could not be measured (examples 3.2 and 4.2).

From the above, it is apparent that the term measuring, as used in this invention, does not include determination of stability of DNA encapsulated nanoparticles. According to the prior art, e.g. Grass et al, the stability of encapsulated DNA is determined by specifying the remaining DNA after exposure to stress. This is not the aim of this invention. Rather, this invention draws conclusions from degradation differences of two sequences to determine a property of interest (such as temperature or light) to which a certain setting (such as a biological matrix or a drilling hole) is/was exposed.

In a forth aspect, the invention relates to novel measuring systems and to novel analytical kits. This aspect of the invention shall be described in further detail below.

Figure 4:
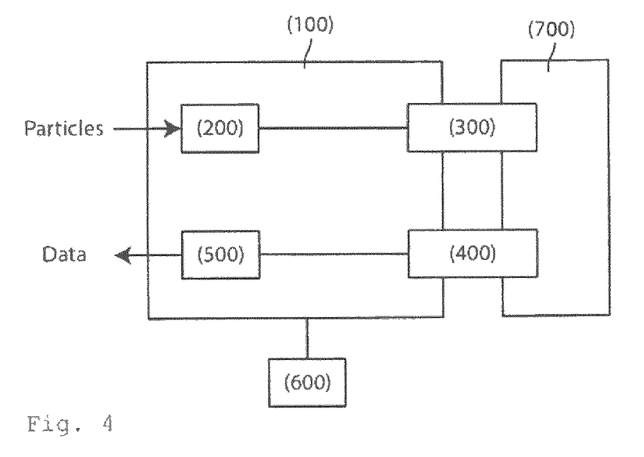
FIG. 4 shows a schematic set up of a measuring device (100) according to the invention, in fluid communication with a setting (700) and controlled by a controlling system (600). Inventive core-shell particles (4) are provided to means for storage (200). Means for distributing said particles (300) are in fluid communication with (200) and the setting of interest (700). Means for collecting (400) said particles (4) are in fluid communication with said setting of interest (700). The samples obtained may be directly transferred to an analytical device (500) or stored and supplied to said device upon demand (not shown). Further indicated are means for controlling (600) system (100) or at least parts thereof.

According to this aspect, the invention provides for a measuring system (100) comprising means for the storage of particles as defined herein (200);
means for distributing said particles in a setting of interest (300);
means for collecting said particles from said setting of interest (400);
means for analyzing said particles (500);
means for controlling said system (600).

These means may be combined in one housing or in more than one housing. Each of these means are known per se, but not yet combined to a measuring system as outlined herein. The measuring system is in fluid communication with a setting (700) where the property of interest is to be determined.

Storage means (200): Suitable are known means for maintaining particles described above in a low viscosity solvent such as water, ethanol, isopropanol and others, in a galenic formulation, or as a solid.

Distributing means (300): Suitable are known means for mixing the particles with the setting of interest. This may be actively done by the use of pumps and valves. This may also be achieved passively, in case a setting of interest is in a flowing stage.

Collecting means (400): Depending on the set-up, commercial centrifuges, magnets, and filters may be used.

Analysing means (500): Commercial qPCR thermal cyclers, such as Roche Lightcycler 96 may be used.

Controlling means (600): Suitably, the system is controlled by a computer, having instructions for running the above means and for providing output data of the measuring results.

Analytical kits: As discussed above, core-shell particles have to be adapted to detect the property of interest. By providing a kit comprising a number of different types of core-shell particles, the end-user may readily select those particles appropriate for a specific situation.

To further illustrate the invention, the following examples are provided. These examples are provided with no intend to limit the scope of the invention.

General: Unless otherwise specified, reagents were used as commercially available.

The following abbreviations are used in this section:

TMAPS—N-trimethoxysilylpropyl-N,N,N-trimethyl-ammonium chloride (50% in methanol)

TEOS—Tetraethoxysilane

EDTA—Ethylenediaminetetraacetic acid

NPOM—6-nitropiperonyloxymethyl

ROS—reactive oxygen species pDADMAC—polydiallyldimethylammonium chloride, MW~200-350 kDa PVPON—poly(vinylpyrrolidone), MW~10 kDa OD—optical density The following nucleic acid sequences are used in this section:

```
Seq.ID No. 1: 103 nt, DAP1, ATCGG GTTAC ACTGG

CTGAC ACTTA TTCTT CAGGT AAGGA CCCCT TATTG GCAGT

GGTGA GTGAG GTTTG GCACT ATCCC TACTA CTGAT GGTCT

TACCC CTGTC GCATG AAT

Seq.ID No. 2: 116 nt, MB1, ATTGC ACCCT TACCA

CGAAG ACAGG TTTGT CCAAT CCCAT ATTGC GACCT TGGCA

GGGGG TTCGC AAGTC CCACC CGAAA CGTTG CTGAA GGCTC

AGGTT TCTGA GCGAC AAAAG C

Seq.ID No. 3: 108 nt, DAP3, TACCG ATGCT GAACA

AGTCG ATGCA GGCTC CCGTC TTTGA AAAGG GGTAA ACATA

CAAGT GGATA GATGA TGGGT AGGGG CCTCC AATAC ATCCA

ACACT CTACG CCC

Seq.ID No. 4: 158 nt, GM-A1, ACACG ACGCT CTTCC

GATCT CGAGC GACAC GACCT AGCAC ATTGA CAATG CTCCG

AGTCC ATGCT CATAA TCTCT CGTCG CCATA CCTGA GAGGC

TGCAG TCCAC CAAGA GGCTA CACAG TCCGC CGCCC GATCT

AGAGA TCGGA AGAGC ACACG TCT
```

```
Seq.ID No. 5: 158 nt, GM-A4, ACACG ACGCT CTTCC

GATCT ATAGG CTAGA AGTGA AGATA GCCAA CAGGC GATGC

AGACC ACGTG AAGAA GTTCC ATCAT ATGGG CGTAT GAGCT

GTGCG AGTCA CACCT AACGC TGTAT CAAAT ATGCC GTTCC

TCAGA TCGGA AGAGC ACACG TCT

Seq.ID No. 6: 158 nt, GM-A7, ACACG ACGCT CTTCC

GATCT CGCCA GTACG GCAGC TTCGG TCTAA CACTA AGAAG

TATGT TGTCT CTGGT GATAC GCCGC CGCAA CCGCC AGCCT

TCTAT GCTCT ATCGT CAGAG TTGCG AGTGA GCAAG ACAGA

GAAGA TCGGA AGAGC ACACG TCT

Seq.ID No. 7: 158 nt, GM-A8, ACACG ACGCT CTTCC

GATCT ACGGT ATGCC ACTTC TGAAT GTGCC CATAC GGTCC

GGCGA CAGCT ATATA GTGAT ACCCT GCGGG CGCTG ACGTA

GTAGG TGGAT GAACT GGTGC AGGAT CGCCA ACAAC AACTG

ATAGA TCGGA AGAGC ACACG TCT

Seq.ID No. 8: 76 nt, GM-02c, ATTGC ACCCT TACCA

CGAAG ACAGG TTTGT CCAAT CCCAT CGTTG CTGAA GGCTC

AGGCT TGGAC CAGCT TTAGT C,

Seq.ID No. 9: 105 nt, JS1, GATTA GCTTG ACCCG

CTCTG TAGGG TCGCG ACTAC GTGAG CTAGG GCTCC GGACT

GGGCT GTATA GTCGA GTCTG ATCTC GCCCC GACAA CTGCA

AACCC CAACT
```

EXAMPLE 1

Encapsulation of Nucleic Acids

This example is divided in two parts, referred to as example 1.1 (non-magnetic core) and 2.2 (magnetic core).

1.1. Encapsulation of Nucleic Acids in Non-Magnetic Particles

Commercial silica particles (~140 nm, Microparticles GmbH) are surface-functionalized with ammonium groups by mixing 1 mL of a 50 mg/mL particle suspension in isopropanol with 10 μL TMAPS (N-trimethoxysilylpropyl-N,N,N-trimethylammonium chloride (50% in methanol)), and stirring overnight (900 rpm) at room temperature. The obtained $SiO_2$-TMAPS particles are washed 3 times with isopropanol and stored at 50 mg/mL. In vitro synthetized mRNA and DNA are bound on the $SiO_2$-TMAPS particles by mixing 1 mL of a solution containing RNA or/and DNA in water (3 μg/mL RNA, 6 μg/mL DNA) with 40 μL of particle suspension, followed by two washing cycles by centrifugation (without using sonication for resuspending the particles) and redispersion in water (0.5 mL). TMAPS (0.5 μL) and TEOS (0.5 μL) are added sequentially to the particle dispersion, vortexing in between. After stirring the mixture for 4 h, additional TEOS (4 μL) is added, and the reaction is run for 4 days at room temperature. The particles are washed twice with isopropanol and can be stored for extended periods of time.

1.2. Encapsulation of Nucleic Acids in Particles with an Iron Oxide Core

To enhance sensor recovery from complex matrices, it is often advantageous to use magnetic sensing particles. To produce such sensing elements, iron oxide particles are incorporated into the core of the sensing element. First, $FeO_x$ particles are synthetized by conventional co-precipitation of $Fe^{2+/3+}$ ions ($Fe^{2+}/Fe^{3+}=1:2$) under alkaline conditions. Four grams of $FeCl_2 \cdot 4H_2O$ (Aldrich, 99%) and 10.8 g of $FeCl_3 \cdot 6H_2O$ (Aldrich, 98%) are dissolved in 50 mL of distilled water. The solution is added dropwise into 500 mL of a 1 M $NH_4OH$ (prepared from Sigma Aldrich, 25%) solution under vigorous stirring at room temperature. The obtained particles are washed five times and stored in water at a concentration of ~50 mg/mL. The freshly prepared iron oxide particles are then functionalized with ammonium groups using TMAPS (50% in MeOH, ABCR GmbH). 1 mL of a 50 mg/mL particle suspension in isopropanol is mixed with 10 µL of TMAPS, and the mixture is stirred overnight (900 rpm) at room temperature. The functionalized particles are washed 3 times and stored in isopropanol at 50 mg/mL. Following this, nucleic acids are bound on the surface of the particles by mixing 1 mL of a solution containing RNA or/and DNA in water (3 µg/mL RNA, 6 µg/mL DNA) with 40 µL of particle suspension, followed by two washing cycles by centrifugation (without using sonication for resuspending the particles) and redispersion in water (0.5 mL). TMAPS (0.5 µL) and TEOS (0.5 µL) are added sequentially to the particle dispersion, vortexing in between. After stirring the mixture for 4 h, additional TEOS (4 µL) is added, and the reaction is run for 4 days at room temperature. The magnetic particles are washed twice with isopropanol and can be stored for extended periods of time.

EXAMPLE 2

Temperature Sensor (DNA/RNA, Inventive)

This example is divided in two parts, referred to as example 2.1 and 2.2. Example 2.1 shows the production and performance of a non-magnetic temperature sensor, whereas example 2.2 presents the magnetic temperature sensor. Furthermore, example 2.2 highlights the importance of a control and a sensing sequence in the same sensing element (vs Alaskar et al)

2.1: Silica-Encapsulated Temperature Sensor (DNA/RNA)

The particles are prepared as in example 1.1 using both RNA (847 nt) and DNA (113 nt, Seq. ID No. 1). Then the particles containing the two nucleic acids are exposed to a source of heat for given amounts of time. As a consequence of the heat, the nucleic acid degrade but at different extent, the RNA (sensing sequence) degrading faster than the DNA (control sequence). Encapsulated RNA and DNA are then released by dissolving the particle with a fluoride containing buffer (0.01 wt % F$^-$ ions in water), purifying using the PCR purification kit (Qiagen), and are further quantified by qPCR. While DNA can be directly analysed by qPCR, RNA is first reverse-transcribed to the complementary DNA. The difference between the quantitative threshold cycle values (defined as the cycle when the amplification curve intersects a threshold line defined by the instrument) obtained for both RNA and DNA ($\Delta C_{qDNA} = C_{qDNA} - C_{qDNA0}$; $\Delta C_{qRNA} = C_{qRNA} - C_{qRNA0}$, where $C_{qDNA0}$ and $C_{qRNA0}$ are the threshold cycles before exposure to the temperature), permits to determine the degradation of the given sequence during the selected time. The difference in $\Delta Cq$ between the DNA and RNA ($\Delta\Delta Cq = \Delta C_{qDNA} - \Delta C_{qRNA}$) allows determining the cumulative temperature $T(t)$ at which the nucleic acids were exposed, by extrapolation from a calibration curve prepared previously ($\Delta\Delta C_q$ vs $T(t)$). In the same way, knowing the temperature, it is possible to estimate the duration t of the exposure to the source of heat, from a degradation curve previously obtained ($\Delta\Delta Cq$ vs t).

The temperature sensor is non-invasive, working on the nanometer-scale, and enables to perform in-situ measurements in areas difficult to access (e.g. in geothermal reservoirs), where the conventional thermometers are ineffective. In addition, this sensor can provide spatially distributed information, while traditional thermometers are only able to record temperature data at single points. The thermometer has an increased temperature upper limit (up to 200° C.) compared to other DNA-based technologies, thanks to the silica protection which slows down nucleic acid degradation and allow them to withstand high temperatures. Furthermore, the sensitivity of the sensor can be tuned by varying the nucleic acid sequences, allowing for accurate measurements across a wide range of temperatures. Two different DNA sequences with different stability can also be used in the place of one DNA and one RNA strand (see example 3.1).

TABLE 1

Encapsulated RNA and DNA were kept at 65° C. and 50% relative humidity for 3 weeks and analysed by qPCR twice per week. Cq and ΔCq values, growing with the time, are reported in the table for both RNA and DNA, as well as the difference in ΔCq between the two (ΔΔCq) at each time point.

| Time (days) | Mean Cq (DNA) | ΔCq (DNA) | Mean Cq (RNA) | ΔCq (RNA) | ΔΔCq |
|---|---|---|---|---|---|
| 0 | 3.03 | 0.00 | 9.96 | 0.00 | 0.00 |
| 3.5 | 5.08 | 2.05 | 12.60 | 2.64 | 0.59 |
| 7 | 5.12 | 2.09 | 14.41 | 4.45 | 2.36 |
| 10.5 | 6.68 | 3.65 | 14.69 | 4.73 | 1.08 |
| 14 | 6.84 | 3.81 | 16.85 | 6.89 | 3.08 |
| 17.5 | 7.53 | 4.50 | 17.67 | 7.71 | 3.21 |
| 21 | 8.31 | 5.28 | 17.87 | 7.91 | 2.63 |

2.2: Magnetic Temperature Sensor (DNA/RNA) (Comparison to Alaskar et al)

The particles are prepared as in example 1.2, using both RNA (847 nt) and DNA (113 nt, Seq. ID No. 1). The prepared magnetic temperature sensor is particularly useful for measuring temperature in large volumes. As a consequence of heat, the nucleic acids degrade but at different extent, the RNA (sensing sequence) degrading faster than the DNA (control sequence).

To recollect the sample from a large volume, magnetic field is applied to upconcentrate the sensing element to a small volume. The sensor particles are then washed 2 times with water, nucleic acids are released and analyzed by PCR, as described in example 2.1.

Table 2 shows the Cq cycles at each temperature. Since the samples are recollected using magnetic separation, the total amount of sample recovered may vary between the samples. Therefore, the trend in DNA decay with increasing temperature is invisible, and the trend of RNA decay is also weak (compare 60° C. vs 65° C.) Therefore, accurate temperature readout is not possible in an open system with only one sequence (where there is no control sequence inside the sensing element, e.g. as presented by Alaskar et al.). This is even more pronounced at the replicate measurements at 70° C., where the total concentrations of each of the two nucleic acids differ by ~1.5 cycles. However, calculating the difference in relative degradation ΔΔCq allows accounting for that.

TABLE 2

Encapsulated RNA and DNA were kept at specified temperatures for 30 min and analysed by qPCR. Cq and ΔCq values are reported in the table for both RNA and DNA, as well as the difference in ΔCq between the two (ΔΔCq) at each time point.

| Temperature (° C.) | Mean Cq (DNA) | ΔCq (DNA) | Mean Cq (RNA) | ΔCq (RNA) | ΔΔCq |
|---|---|---|---|---|---|
| 50 | 11.64 | 0.00 | 17.13 | 0.00 | 0.00 |
| 55 | 11.34 | −0.30 | 17.81 | 0.68 | 0.98 |
| 60 | 12.76 | 1.12 | 22.36 | 5.23 | 4.11 |
| 65 | 11.53 | −0.11 | 22.33 | 5.20 | 5.31 |
| 70 | 14.06 | 2.42 | 26.11 | 8.98 | 6.56 |
| 70 | 12.44 | 0.80 | 24.61 | 7.48 | 6.68 |
| 75 | 12.49 | 0.85 | 29.35 | 12.22 | 11.37 |

EXAMPLE 3, COMPARATIVE

Temperature Sensor (Two Distinct DNA) and Control Experiments with Unsuitable Sequences This example is divided in three parts, referred to as example 3.1, 3.2, and 3.3.

3.1: Temperature Sensor (Two Distinct DNA, Inventive)

The particles are prepared as in example 1.1 using two different types of DNA: DAP1 (113 nt, Seq. ID No. 1) and MB1: (116 nt, Seq. ID No. 2). Then the particles containing the two nucleic acids are exposed to different temperatures for 2.5 h. As a consequence of heat, the nucleic acids degrade, but to a different extent, the MB1 (sensing sequence) degrading faster than the DAP3 (control sequence). Encapsulated DNA sequences are then released as described in example 2.1, amplified by PCR, and the threshold cycles are obtained in an analogous way. The difference between the quantitative threshold cycle values permits to determine the degradation of the given sequence during the selected time. Only the difference in ΔCq between the DAP1 (control sequence) and MB1 (sensing sequence) ($\Delta\Delta Cq = \Delta Cq_{MB1} - \Delta Cq_{DAP1}$) allows determining the cumulative temperature T(t) at which the nucleic acids were exposed, by extrapolation from a calibration curve prepared previously (ΔΔCq vs T(t)).

TABLE 3

Encapsulated DAP1 (control sequence) and MB1 (sensing sequence) were kept at various temperatures for 2.5 h and analysed by qPCR. Cq and ΔCq values are reported in the table for both sequences, as well as the difference in ΔCq between the two (ΔΔCq) at each time point.

| Temperature (° C.) | Mean Cq (DAP1) | ΔCq (DAP1) | Mean Cq (MB1) | ΔCq (MB1) | ΔΔCq |
|---|---|---|---|---|---|
| 60 | 5.05 | 0.00 | 7.71 | 0.00 | 0.00 |
| 80 | 10.27 | 5.22 | 14.70 | 6.99 | 1.77 |
| 100 | 18.28 | 13.23 | 24.87 | 17.16 | 3.93 |
| 120 | 28.40 | 23.35 | 39.02 | 31.31 | 7.96 |

3.2: Comparison to Prior Art (Grass et al)

In this example, known particles were attempted to be used as a temperature sensor. The known particles are described in example 16 of Grass et al (WO2013/143014). These known particles contain a known amplicon (pBluescript II KS, MCS, 238 bp) mixed with a standard DNA Ladder (Invitrogen DNA ladder Plus), ratio 1:30.

Upon repeating the thermal treatment of example 3.1 with these particles, it was realized that the DNA ladder was not possible to amplify. The reason is that PCR amplification requires the knowledge about the sequence of the DNA, which in this case is not publicly available. Furthermore, the ladder contains a large number of different sequences. Thus, even if there was an imaginary amplification mechanism, it would be not clear which of the many sequences to amplify. This further demonstrates that the DNA ladder in example 16 of Grass et al served as a filler rather than as an actual DNA to quantify. Without the possibility of amplification, the extent of degradation could not be determined (Table 4).

TABLE 4

Two types of encapsulated DNA (pBluescript II KS, MCS and DNA Ladder) were kept at various temperatures for 2.5 h and analysed by qPCR. Cq and ΔCq values are reported in the table for pBluescript II, but not for the DNA ladder, because it could not be measured.

| Temp. (° C.) | Mean Cq (pBluescript II) | ΔCq (pBluescript II) | Mean Cq (DNA ladder) | ΔCq (DNA ladder) | ΔΔCq |
|---|---|---|---|---|---|
| 60 | 19.92 | 0.00 | — | — | — |
| 80 | 22.27 | 2.35 | — | — | — |
| 100 | 29.41 | 9.49 | — | — | — |
| 120 | —* | —* | — | — | — |

The difference in ΔCq between the two (ΔΔCq) at each time point could consequently not be determined. The asterisk (*) marks that the concentration of the sequence was below the negative control limit.

3.3: Comparative Example (Temperature Readout with Different Sensor Concentrations (Comparison to Alaskar et al.)

The particles are prepared as in example 1.1 using two different types of DNA: DAP1 (113 nt, Seq. ID No. 1) and MB1 (116 nt, Seq. ID No. 2). Then the particles containing the two nucleic acids are put into various volumes of water (=different final sensor concentrations) and are exposed to different temperatures for 2.5 h. As a consequence of heat, the nucleic acids degrade, but to a different extent, the MB1 (sensing sequence) degrading faster than the DAP3 (control sequence). Encapsulated DNA sequences are then released as described in example 2.1, amplified by PCR, and the threshold cycles are obtained in an analogous way. The difference between the quantitative threshold cycle values permits to determine the degradation of the given sequence during the selected time. Only the difference in ΔCq between the DAP1 (control sequence) and MB1 (sensing sequence) ($\Delta\Delta Cq = \Delta Cq_{MB1} - \Delta Cq_{DAP1}$) allows determining the cumulative temperature T(t) at which the nucleic acids were exposed, by extrapolation from a calibration curve prepared previously (ΔΔCq vs T(t)).

TABLE 5

Encapsulated DAP1 (control sequence) and MB1 (sensing sequence) were kept at various temperatures and concentrations for 2.5 h and analysed by qPCR. C and ΔCq values are reported in the table for both RNA and DNA, as well as the difference in ΔCq between the two (ΔΔCq) at each time point.

| Sensor conc. (μg/mL) | Temp. (° C.) | Mean Cq (DAP1) | ΔCq (DAP1) | Mean Cq (MB1) | ΔCq (MB1) | ΔΔCq |
|---|---|---|---|---|---|---|
| 10 | 60 | 5.05 | 0.00 | 7.71 | 0.00 | 0.00 |
| 10 | 80 | 10.27 | 5.22 | 14.70 | 6.99 | 1.77 |
| 10 | 100 | 18.28 | 13.23 | 24.87 | 17.16 | 3.93 |
| 0.2 | 60 | 10.50 | 5.45 | 13.18 | 5.47 | 0.02 |
| 0.2 | 80 | 15.78 | 10.73 | 20.19 | 12.48 | 1.75 |
| 0.2 | 100 | 23.84 | 18.79 | 30.48 | 22.77 | 3.98 |

As can be seen from Table 5, ΔΔCq between the two nucleic acids decays over time irrespective of sample concentration (i.e. if the ΔΔCq≈1.76, irrespective of the concentration it is clear that the sample has experienced 80° C.).

It is not the case for each of the two nucleic acids separately: if the mean Cq of DAP1 is detected to be ~10.5, it is not clear whether it is a higher concentration sample at 80° C., or a lower concentration sample at 60° C., or anything in between.

Since typically the setting to be measured is not perfectly closed, or the recovery concentration or efficiency are not perfect (e.g. from an underground reservoir), a particle with only one nucleic acid would not yield a useful sensor. Introducing a second type of nucleic acid into the same sensing element excludes such uncertainty, because a single sensing element (i.e. particle) serves as a complete sensing element.

EXAMPLE 4

DNA Sequences that Possess Significantly Different Stability Towards a Property of Interest This example is divided in two parts, referred to as example 4.1, and 4.2.

4.1: Two Distinct Sequences with Different Thermal Stability

From a large library screening, the two following solutions of DNA are prepared at 0.5 ug/mL in 1× Tris-EDTA buffer (pH=8): the first solution contains GM-A1 (158 nt, Seq. ID No. 4); the second solution contains GM-A4 (158 nt, Seq. ID No. 5). Each of the solutions is aliquoted to the volume of 10 μL in 20 tubes, and the tubes are left open overnight to dry. The dried out DNA is then kept at 65° C. and 50% relative humidity (achieved by keeping a saturated solution of sodium bromide in the same container as the tubes). The tubes of each DNA are taken out in triplicates at chosen times (see Table 6). 200 uL of MilliQ water are added to each tube, it is vortexed to redissolve DNA and the samples are subjected to PCR. The obtained difference in ΔCq values in PCR would then have to be compared to the reference scale and the cumulative temperature T(t) can be calculated analogously to the example 2.1.

TABLE 6

Both specifically adapted nucleic acids (GM-A1 and GM-A4) were kept at 65° C. and 50% relative humidity for 9 days and analysed by qPCR twice per week. Cq and ΔCq values are reported in the table for both sequences, as well as the difference in ΔCq between the two (ΔΔCq) at each time point.

| Time (hours) | Mean Cq (GM-A1) | ΔCq (GM-A1) | Mean Cq (GM-A4) | ΔCq (GM-A4) | ΔΔCq |
|---|---|---|---|---|---|
| 0 | 7.43 | 0.00 | 4.80 | 0.00 | 0.00 |
| 2 | 10.73 | 3.30 | 10.10 | 5.30 | 2.00 |
| 6 | 14.70 | 7.27 | 16.64 | 11.84 | 4.57 |
| 9 | 16.97 | 9.54 | 19.80 | 15.00 | 5.46 |

4.2: Two Distinct Sequences with Approximately the Same Thermal Stability

Two sequences with an identical length and primer design as in example 4.1 are randomly generated. As a consequence of the same sensitivity towards a property of interest, they are not sensing sequence and control sequence, as discussed in this invention: GM-A7 (158 nt, Seq. ID No. 6) and GM-A8 (158 nt, Seq. ID No. 7).

Identically to example 4.1, solutions of each of the two sequences are prepared at 0.5 ug/mL in 1× Tris-EDTA buffer (pH=8). Each of the solutions is aliquoted to the volume of 10 μL in 20 tubes, and the tubes are left open overnight to dry. The dried out DNA is then kept at 65° C. and 50% relative humidity (achieved by keeping a saturated solution of sodium bromide in the same container as the tubes). The tubes (serving as replacements for particle encapsulation) of each DNA are taken out in triplicates at chosen times (see Table 7). 200 uL of MilliQ water are added to each tube, it is vortexed to redissolve DNA and the samples are subjected to PCR. The obtained differences in ΔCq values in PCR are displayed in Table 7 below. They however do not follow any trend because the two sequences are not intentionally adapted to degrade to different extents, and therefore cannot be used as a temperature sensor. This contrasts the specifically adapted sequences in example 4.1, that would allow measuring temperature T(t).

TABLE 7

Two random DNA sequences (GM-A7 and GM-A8) were kept at 65° C. and 50% relative humidity for 21 days and analysed by qPCR at indicated time points. Cq and ΔCq values are reported in the table for both sequences, as well as the difference in ΔCq between the two (ΔΔCq) at each time point.

| Time (days) | Mean Cq (GM-A7) | ΔCq (GM-A7) | Mean Cq (GM-A8) | ΔCq (GM-A8) | ΔΔCq |
|---|---|---|---|---|---|
| 0 | 5.69 | 0.00 | 5.90 | 0.00 | 0.00 |
| 4 | 11.94 | 6.25 | 12.31 | 6.41 | 0.16 |
| 8 | 13.57 | 7.88 | 14.17 | 8.27 | 0.39 |
| 14 | 15.68 | 9.99 | 15.73 | 9.83 | −0.16 |
| 21 | 17.09 | 11.40 | 17.38 | 11.48 | 0.08 |

EXAMPLE 5

Light Sensor 6-nitropiperonyloxymethylene (NPOM)-caged 76 nt DNA (GM02c, Seq. ID No. 8 with three thymine bases in the primer area of each strand caged with NPOM, available commercially from Glen Research, ~99% caged, 1% uncaged) is encapsulated in TMAPS-modified silica as described in example 1.1. The DNA sequence serves as a control, while the NPOM-caged DNA serves as the sensing sequence. The prepared sensor can detect 18 W UVA (365 nm) light up to 60 min.

Readout is performed by dissolving silica encapsulation with a fluoride containing buffer (0.01 wt % F⁻ ions in water) followed by purifying using the PCR purification kit (Qiagen), and preparing PCR samples in duplicates: one sample is irradiated with 60 W UVA lamp for 10 min followed by PCR, whereas the other is subjected directly to PCR. The obtained difference in ΔCq values between non-irradiated DNA (sensing seq.) and irradiated DNA (control seq.) ($\Delta\Delta Cq = \Delta C_{q-UV} - \Delta C_{q+UV}$) allows determining the cumulative irradiation when compared to the reference scale and the amount of irradiation is calculated as described in example 2.1.

TABLE 8

Encapsulated NPOM-caged DNA was irradiated with an 18 W UVA lamp at 65 cm distance. The samples were removed from the light, dissolved and analysed by qPCR in duplicates (one sample as obtained, the other after treating with a 60 W UVA lamp for 10 min). Cq and ΔCq values as well as the difference between the two samples (ΔΔCq) are reported at each time point.

| Time (hh:mm) | Mean Cq (+UV) | ΔCq (+UV) | Mean Cq (−UV) | ΔCq (−UV) | ΔΔCq |
| --- | --- | --- | --- | --- | --- |
| 00:00 | 10.19 | 0.00 | 12.75 | 0.00 | 0.00 |
| 00:01 | 10.52 | 0.33 | 12.87 | 0.12 | −0.21 |
| 00:02 | 9.40 | −0.79 | 11.55 | −1.20 | 0.41 |
| 00:05 | 8.24 | −1.95 | 9.67 | −3.08 | 1.13 |
| 00:10 | 8.48 | −1.71 | 9.43 | −3.32 | 1.61 |
| 00:30 | 7.02 | −3.17 | 7.60 | −5.15 | 1.98 |
| 01:00 | 5.69 | −4.50 | 5.86 | −6.89 | 2.39 |

EXAMPLE 6

Oxidative Stress Sensor

This example is divided in two parts, referred to as example 6.1 and 6.2.

6.1: Oxidative Stress Sensor (Inventive)

A 108 nt DNA (DAP3, 108 nt, Seq. ID No. 3) is encapsulated in $SiO_2$ as follows: 35 uL of TMAPS-modified $SiO_2$ (~150 nm, 50 mg/mL in isopropanol, prepared as in example 1.1) and 20 uL of DAP3 solution (500 ug/mL in water) are added to an Eppendorf tube containing 1 mL water. The solution is vortexed and allowed to stay at rt for 2 min for the DNA to bind TMAPS-modified silica. Following that, the solution is centrifuged for 3 min at 21000 g. The supernatant is decanted and the concentration of remaining DNA is quantified using Qubit. The pellet is washed once with water, centrifuged again and dispersed in 0.5 mL aqueous pDADMAC solution (polydiallyldimethyl-ammonium chloride MW~200-350 kDa, 1 mg/mL). The tube is shaken for 20 min at rt, centrifuged, and the pellet is washed twice with water. Following that, the pellet is dispersed in 1 mL PVPON solution (poly(vinylpyrrolidone) MW~10 kDa, 0.1 mg/mL) and shaken for 20 min at rt. The solution is centrifuged, the supernatant decanted, and the pellet washed twice with water and once with ethanol. To produce the ROS-resistant coating for DAP3, the pellet is dispersed in a solution containing 233 uL ethanol, 72 uL milliQ water, 22.1 uL TEOS, and 5 uL acetic acid solution (10M in water). The tube is left shaking at 900 rpm at rt overnight. Next day it is washed twice with water and ethanol to obtain DAP3 encapsulated in a ROS-resistant coating.

The produced particles are then dispersed in 500 uL isopropanol containing 2.5 uL TMAPS (50% in methanol). The tube is shaken overnight to produce TMAPS-modified surface. The solution is centrifuged, washed with isopropanol and water, and encapsulation of the second DNA strand (JS1, 105 nt, Seq. ID No. 9) is done exactly as described above including subsequent addition of pDADMAC and PVP. After PVPON addition, the pellet is again washed twice with water and once with ethanol. The porous encapsulation is produced by dispersing the pellet in 600 uL ethanol containing 24 uL 25% ammonium hydroxide solution and 2 uL TEOS and shaking the obtained solution overnight at rt.

The harsh ROS stress is induced by treating 5 uL of the prepared particles (2 mg/mL) with a solution consisting of 12.5 uL $CuCl_2$ (500 μM), 12.5 uL $H_2O_2$ (20 mM), and 2.5 uL L-ascorbic acid (20 mM) for 5 minutes. After this time, the radicals are quenched by adding 17.5 uL EDTA (100 mM). The particles are then dissolved and the DNA is recovered using PCR purification kit (Qiagen). Each of the two sequences is quantified by PCR using appropriate primer sets. The results are presented in Table 9.

TABLE 9

Encapsulated DNA (2 sequences in distinct compartments) were treated with a ROS as described, and then dissolved and analysed by qPCR. Cq and ΔCq values are reported in the table for each of the sequences, as well as the difference in ΔCq between the two (ΔΔCq) at before and after the ROS stress.

| ROS stress | Mean Cq (DAP3) | ΔCq (DAP3) | Mean Cq (JS1) | ΔCq (JS1) | ΔΔCq |
| --- | --- | --- | --- | --- | --- |
| No | 4.66 | 0.00 | 8.22 | 0.00 | 0.00 |
| Yes | 9.56 | 4.90 | 15.23 | 7.01 | 2.11 |

6.2: Oxidative Stress (Control Experiment)

Nine solutions of free annealed DNA (Arch1, a mixture of random sequences of a length of 158 nt) are prepared in milliQ water at a concentration of 50 ng/mL. Three of them are kept as controls for 72 h at +4° C., three others are stored at 65° C. under normal atmosphere for 72 h. Further three solutions are first bubbled with argon and then stored under argon atmosphere for 72 h. Another three solutions are prepared in at the same concentration in 1 mM EDTA, and stored as well at 65° C. under normal atmosphere for 72 h. The concentrations of the intact DNA are quantified by PCR. When DNA is treated under argon atmosphere, no significant degradation is observed. Under EDTA radical quencher, DNA degradation is visible, but controlled. Under oxidative conditions, DNA is completely degraded over the reaction time. (negative Cq=31.77).

TABLE 10

The degradation results of stress induced on free DNA in water. Cq values are reported in the table for each condition, as well as the difference in Cq between the condition and the control at each time point.

| Condition | Mean Cq (Arch) | ΔCq |
|---|---|---|
| Control (4° C.) | 4.87 | 0.00 |
| O₂ (65° C.) | 32.94 | 28.07 |
| Ar (65° C.) | 4.75 | −0.12 |
| EDTA (65° C.) | 7.42 | 3.60 |

EXAMPLE 7 pH Sensor

This example is divided in two parts, referred to as example 7.1 and 7.2.

7.1: pH Sensor (DNA/RNA) (Inventive)

The particles are prepared as in example 2.1 using both RNA (847 nt) and DNA (113 nt). Then the particles containing the two nucleic acids are exposed to solutions with different pH values. As a consequence of proton concentration (pH), the nucleic acids degrade but to a different extent, the RNA (sensing sequence) degrading faster than the DNA (control sequence). Encapsulated RNA and DNA are then released by dissolving the particle with a fluoride containing buffer (0.01 wt % F⁻ ions in water), purifying using the PCR purification kit (Qiagen), and are further quantified by qPCR. While DNA can be directly analysed by qPCR, RNA is first reverse-transcribed to the complementary DNA. The difference between the quantitative threshold cycle values (defined as the cycle when the amplification curve intersects a threshold line defined by the instrument) obtained for both RNA and DNA ($\Delta C_{qDNA} = C_{qDNA} - C_{qDNA0}$; $\Delta C_{qRNA} = C_{qRNA} - C_{qRNA0}$, where $C_{qDNA0}$ and $C_{qRNA0}$ are the threshold cycles before exposure to various pH), permits to determine the degradation of the given sequence during the selected time (Table 11).

The difference in ΔCq between the DNA and RNA ($\Delta\Delta Cq = \Delta C_{qDNA} - \Delta C_{qRNA}$) allows determining the pH to which the nucleic acids were exposed, by extrapolation from a calibration curve prepared previously ($\Delta\Delta C_q$ vs pH(t)). In the same way, knowing the pH, it is possible to estimate the duration t of the exposure to it, from a previously obtained degradation curve (ΔΔCq vs t).

The pH sensor is non-invasive, working on the nanometer-scale, and enables to perform in-situ measurements in areas difficult to access (e.g. in geothermal reservoirs, or single cells), where the conventional pH meters are ineffective. In addition, this sensor can provide spatially distributed information, while traditional pH meters are only able to record pH at single points. The sensitivity of the sensor can be tuned by varying the nucleic acid sequences and coating thickness/structure, allowing for accurate measurements across a range of pH.

TABLE 11

Encapsulated RNA and DNA were kept in the aqueous solutions with the above specified pH for 30 min, centrifuged, washed with water, and analysed by qPCR. Cq and ΔCq values are reported in the table for both RNA and DNA, as well as the difference in ΔCq between the two (ΔΔCq) at each pH value.

| pH | Mean Cq (DNA) | ΔCq (DNA) | Mean Cq (RNA) | ΔCq (RNA) | ΔΔCq |
|---|---|---|---|---|---|
| 7.2 | 9.94 | 0.00 | 18.64 | 0.00 | 0.00 |
| 9.7 | 9.55 | −0.39 | 18.28 | −0.36 | −0.03 |
| 11.7 | 10.02 | 0.08 | 19.89 | 1.25 | 1.17 |
| 13.0 | 10.43 | 0.49 | 25.46 | 6.82 | 6.33 |

7.2: pH Sensor (Control, with Non-Adapted Sequences)

The experiment is performed identically to example 7.1, only with different nucleic acids. In this case, two nucleic acids are not adapted to degrade differently to pH: DAP3 (108 nt, Seq. ID No. 3) and JS1: (105 nt, Seq. ID No. 9).

The two nucleic acids are encapsulated in a silica particle as in example 6.1. Then the particles containing the two nucleic acids are exposed to solutions with different pH values. Encapsulated DNAs are then released by dissolving the particle with a fluoride containing buffer (0.01 wt % F⁻ ions in water), purifying using the PCR purification kit (Qiagen), and are further quantified by qPCR. The difference between the quantitative threshold cycle values obtained for both DNA sequences ($\Delta C_{qDAP3} = C_{qDAP3} - C_{qDAP3-t0}$; $\Delta C_{qJS1} = C_{qJS1} - C_{qJS1-t0}$, where $C_{qDAP3-t0}$ and $C_{qJS1-t0}$ are the threshold cycles before exposure to various pH), permits to determine the degradation of the given sequence during the selected time.

Since in contrast to ex. 7.1 the sequences are not adapted to degrade more or less towards the property of interest, the difference in ΔCq between the two sequences ($\Delta\Delta Cq = \Delta C_{qDAP3} - \Delta C_{qJS1}$), does not allow determining the pH to which the nucleic acids were exposed:

TABLE 12

Encapsulated DNA were kept in the aqueous solutions with the above specified pH for 30 min, centrifuged, washed with water, and analysed by qPCR. Cq and ΔCq values, growing with pH, are reported in the table for both RNA and DNA, as well as the difference in ΔCq between the two (ΔΔCq) at each pH value. No significant difference in degradation of the two was observed.

| pH | Mean Cq (DAP3) | ΔCq (DAP3) | Mean Cq (JS1) | ΔCq (JS1) | ΔΔCq |
|---|---|---|---|---|---|
| 7.2 | 10.24 | 0.00 | 18.04 | 0.00 | 0.00 |
| 9.7 | 10.28 | 0.04 | 18.15 | 0.11 | 0.07 |
| 11.7 | 10.71 | 0.47 | 18.56 | 0.52 | 0.05 |
| 13.0 | 9.91 | −0.33 | 17.74 | −0.30 | −0.03 |

Furthermore, when compared to example 6.1, it becomes obvious that the suggested encapsulated sequences (DAP3 and JS1) serve as a sensor for ROS, but have similar stability towards a different kind of stress (namely, pH). Prior art (Alaskar et al.) did not have such a compensation system.

EXAMPLE 8

Measuring a Property of Interest Inside a Living Organism

The light sensor particles are prepared as in example 5 using NPOM-caged DNA. The particles are mixed with E.

coli and are added to three plates containing identical concentrations (~500 cells/mL) of *Paramecium Caudatum* culture. The final concentration of 1 µg/mL of the sensors particles, an $OD_{600}$ of 0.25 of *E. coli* in the *paramecia* cultures are obtained. After *E. coli*/sensor particle uptake in *paramecia* for 8 h in the dark, one plate is left in the dark, one is irradiated with solar simulator for 10 min (20 W/m$^2$), and another for 2 h (20 W/m$^2$). For each time point (light: 0 min; 10 min; 2 h) 1 mL of culture is filtered with a 5.0 µm hydrophilic syringe filter to wash away the particles that did not get uptaken. The *paramecia* are then washed with tap water (5 mL), and released in culture medium (0.5 mL). Single *paramecia* are collected with a micropipette (0.75 µL) under a light microscope and are put in 200 µL tap water to wash away any sensor particles sticking to the surface, followed by transferring single *paramecia* (0.75 µL) to individual PCR tubes containing 20 µL of PCR-grade water. For each cell, a control sample from the washing solution with the same volume is prepared the same way. After collecting 20 single cells and 20 control samples for each data point, the samples were heat-treated at 95° C. for 10 min to lyse the cells and release the sensor. Following this, 2 µL of 1:10 BOE solution was added and the tubes were shaken for 10 min. Next, PCR reactions are prepared for each sample in duplicates using qPCR as described in example 5. The difference in the obtained threshold cycle numbers ($\Delta Cq = Cq_{(-UV)} - Cq_{(+UV)}$) is converted to the relative concentration of the caged DNA ($c_{rel} = 1 - c_{(-UV)}/c_{(+UV)} = 1 - 2^{Cq(-UV) - Cq(+UV)} = 1 - 2^{\Delta Cq}$).

As can be seen from the Table 13 below, the three irradiation times can be clearly distinguished from one another. This proves that the light sensor can be used to determine properties inside single cells or microorganisms in a reliable and uncomplicated setup. The same technique could be used to measure other properties of interest inside living organisms or other very small volumes.

TABLE 13

Sensor particles, uptaken by *Paramecium Caudatum*, were extracted, DNA released by a fluoride-containing buffer, and analysed by qPCR as described in example 5. Cq and ΔCq values are reported in the table for both sensing (-UV) and control (+UV) sequences, as well as the difference between the two (ΔCq) at each data point. The threshold cycles are further converted to relative concentration of the caged DNA (-UV), showing a clear decline in caged DNA with irradiation time.

| Light duration | Mean Cq (+UV) | Mean Cq (-UV) | ΔCq | Fraction caged |
|---|---|---|---|---|
| 0 min | 27.97 | 31.23 | 3.26 | 0.91 |
| 10 min | 28.46 | 30.16 | 1.70 | 0.72 |
| 120 min | 29.24 | 30.00 | 0.76 | 0.36 |

The invention claimed is:

1. Core-shell particles, comprising particles having a primary particle size of 10-10000 nm, wherein
   the core comprises a first and a second group of nucleic acids,
   the shell comprises an inorganic material or an organic material, wherein
   said first group of nucleic acids comprises a sensing sequence adapted to degrade upon exposure to a property of interest and
   said second group of nucleic acids comprises a control sequence adapted to degrade less upon exposure to this property of interest; and
   the relative concentration ($c_{final}/c_0$) of the sensing sequence left after the said exposure is at least 15% ($\Delta\Delta Cq=\sim 0.23$ cycles) lower than that of the control sequence; and
   said sensing sequence and control sequence are measurable by nucleic acid amplification methods.

2. The core-shell particles according to claim 1, wherein said amplification method is selected from PCR, qPCR, LAMP, SDA, and HDA.

3. The core-shell particles according to claim 1, wherein
   (a) said sensing sequence and control sequence are located within one single core; or
   (b) said sensing sequence and control sequence are located in separate cores and a signalling molecule is located in the same core as the sensing sequence; or
   (c) said control sequence is located in an inner core, surrounded by a shell inert towards the property of interest and said sensing sequence is located in an outer core, surrounded by a shell permeable/susceptive towards the property of interest; or
   (d) said control sequence is located in an inner core, surrounded by a shell inert towards the property of interest and said sensing sequence is located in an outer core, surrounded by a shell degrading upon exposure of the property of interest.

4. The core-shell particles according to claim 1, wherein said first and second group of nucleic acids
   are selected from the group of DNA and/or RNA;
   are natural and/or synthetic and/or chemically modified; and/or
   have a length between 50-5000 nucleotides.

5. The core-shell particles according to claim 1, wherein the sequences of said two or more nucleic acids differ by five or more nucleotides.

6. The core-shell particles according to claim 1, wherein the shell comprises
   silica; or
   silica comprising an additional inorganic coating; or
   silica with surface functionalization that consists of organic molecules; or
   a polymeric coating.

7. The core-shell particles according to claim 1, wherein the core further comprises magnetic material in the form of small particles.

8. The core-shell particles according to claim 7, wherein said magnetic material has soft magnetic properties.

9. A method for measuring a property of interest in a setting, said method comprising the steps of
   (a) providing core shell particles;
   (b) distributing said particles in said setting and thereby exposing them to the property of interest;
   (c) collecting said particles; and
   (d) analysing said particles;
   wherein said core-shell particles comprise primary particles having a primary particle size of 10-10000 nm, wherein
   the shell comprises an inorganic material or an organic material,
   the core comprises a first and a second group of nucleic acids, whereby
   said first group of nucleic acids comprises a sensing sequence adapted to degrade upon exposure to a property of interest, and
   said second group of nucleic acids comprises a control sequence adapted to degrade less upon exposure to this property of interest.

10. The method of claim 9, wherein analysing of said particles is performed by a nucleic acid amplification method.

11. The method of claim 9, wherein said setting is selected from matrices of biological origin; settings in mining, energy and water supply and recycling industries; environmental settings; and polymers.

12. The method of claim 11, wherein said matrix of biological origin is selected from cells, living organisms, blood and other body fluids.

13. The method of claim 9, wherein said property of interest is
   a chemical property of interest selected from pH, oxidative stress, humidity, reduction potential, genotoxicity, chemical reactivity, metal ion content, microbial activity, and metabolic activity; and / or
   a physical property of interest selected from exposure to temperature, electro-magnetic radiation, and radioactive radiation.

14. The method of claim 9, wherein
   said step (a) comprises preparing a dispersion of said core-shell particles in an aqueous or non-aqueous low-viscosity liquid, in a galenic formulation, or as a solid; and/or
   said step (b) comprises mixing the dispersion with the medium in which the property is to be measured; and/or in said step (c) the collection of particles is effected by (c1) applying a magnetic field or (c2) centrifugation; and/or said step (d) comprises (d1) liberating said nucleic acids from said particle by use of a fluoride ion containing aqueous solution and (d2) subjecting the thus obtained nucleic acid solution to an amplification reaction and (d3) detecting the concentration of two or more nucleic acid sequences.

15. A method for measuring a property of interest in a setting, said method comprising the steps of
    (a) providing core shell particles;
    (b) distributing said particles in said setting and thereby exposing them to the property of interest;
    (c) collecting said particles; and
    (d) analysing said particles;
    wherein said core-shell particles are as defined in claim 1.

16. The method of claim 15, wherein analysing of said particles is performed by a nucleic acid amplification method.

17. The method of claim 15, wherein said setting is selected from matrices of biological origin; settings in mining, energy and water supply and recycling industries; environmental settings; and polymers.

18. The method of claim 17, wherein said matrix of biological origin is selected from cells, living organisms, blood and other body fluids.

19. The method of claim 15, wherein said property of interest is
    a chemical property of interest selected from pH, oxidative stress, humidity, reduction potential, genotoxicity, chemical reactivity, metal ion content, microbial activity, and metabolic activity; and/or
    a physical property of interest selected from exposure to temperature, electro-magnetic radiation, and radioactive radiation.

20. The method of claim 15, wherein
    said step (a) comprises preparing a dispersion of said core-shell particles in an aqueous or non-aqueous low-viscosity liquid, in a galenic formulation, or as a solid; and/or
    said step (b) comprises mixing the dispersion with the medium in which the property is to be measured; and/or
    in said step (c) the collection of particles is effected by (c1) applying a magnetic field or (c2) centrifugation; and/or
    said step (d) comprises (d1) liberating said nucleic acids from said particle by use of a fluoride ion containing aqueous solution and (d2) subjecting the thus obtained nucleic acid solution to an amplification reaction and (d3) detecting the concentration of two or more nucleic acid sequences.

21. A measuring system comprising
    means for storage of particles, containing particles as defined in claim 1;
    means for distributing said particles in a setting of interest;
    means for collecting said particles from said setting of interest;
    means for analysing said particles; and
    means for controlling said system.

* * * * *

SEQUENCE LISTING

```
<160> NUMBER OF SEQ ID NOS: 9

<210> SEQ ID NO 1
<211> LENGTH: 113
<212> TYPE: DNA
<213> ORGANISM: Artificial
<220> FEATURE:
<223> OTHER INFORMATION: DAP1

<400> SEQUENCE: 1
atcgggttac actggctgac acttattctt caggtaagga ccccttattg gcagtggtga      60
gtgaggtttg gcactatccc tactactgat ggtcttaccc ctgtcgcatg aat            113

<210> SEQ ID NO 2
<211> LENGTH: 116
<212> TYPE: DNA
<213> ORGANISM: Artificial
<220> FEATURE:
<223> OTHER INFORMATION: MB1

<400> SEQUENCE: 2
attgcaccct taccacgaag acaggtttgt ccaatcccat attgcgacct tggcagggg       60 ttcgcaagtc ccacccgaaa cgttgctgaa ggctcaggtt tctgagcgac aaaagc         116

<210> SEQ ID NO 3
<211> LENGTH: 108
<212> TYPE: DNA
<213> ORGANISM: Artificial
<220> FEATURE:
<223> OTHER INFORMATION: DAP3

<400> SEQUENCE: 3
taccgatgct gaacaagtcg atgcaggctc ccgtctttga aaaggggtaa acatacaagt     60
ggatagatga tgggtagggg cctccaatac atccaacact ctacgccc                 108
```

```
<210> SEQ ID NO 4
<211> LENGTH: 158
<212> TYPE: DNA
<213> ORGANISM: Artificial
<220> FEATURE:
<223> OTHER INFORMATION: GM-A1

<400> SEQUENCE: 4
acacgacgct cttccgatct cgagcgacac gacctagcac attgacaatg ctccgagtcc      60
atgctcataa tctctcgtcg ccatacctga gaggctgcag tccaccaaga ggctacacag     120
tccgccgccc gatctagaga tcggaagagc acacgtct                             158

<210> SEQ ID NO 5
<211> LENGTH: 158
<212> TYPE: DNA
<213> ORGANISM: Artificial
<220> FEATURE:
<223> OTHER INFORMATION: GM-A4

<400> SEQUENCE: 5
acacgacgct cttccgatct ataggctaga agtgaagata gccaacaggc gatgcagacc      60
acgtgaagaa gttccatcat atgggcgtat gagctgtgcg agtcacacct aacgctgtat     120
caaatatgcc gttcctcaga tcggaagagc acacgtct                             158

<210> SEQ ID NO 6
<211> LENGTH: 158
<212> TYPE: DNA
<213> ORGANISM: Artificial
<220> FEATURE:
<223> OTHER INFORMATION: GM-A7

<400> SEQUENCE: 6
acacgacgct cttccgatct cgccagtacg gcagcttcgg tctaacacta agaagtatgt      60
tgtctctggt gatacgccgc cgcaaccgcc agccttctat gctctatcgt cagagttgcg     120
agtgagcaag acagagaaga tcggaagagc acacgtct                             158

<210> SEQ ID NO 7
<211> LENGTH: 158
<212> TYPE: DNA
<213> ORGANISM: Artificial
<220> FEATURE:
<223> OTHER INFORMATION: GM-A8

<400> SEQUENCE: 7
acacgacgct cttccgatct acggtatgcc acttctgaat gtgcccatac ggtccggcga      60
cagctatata gtgataccct gcgggcgctg acgtagtagg tggatgaact ggtgcaggat     120
cgccaacaac aactgataga tcggaagagc acacgtct                             158

<210> SEQ ID NO 8
<211> LENGTH: 76
<212> TYPE: DNA
<213> ORGANISM: Artificial
<220> FEATURE:
<223> OTHER INFORMATION: GM-02c

<400> SEQUENCE: 8
attgcaccct taccacgaag acaggtttgt ccaatcccat cgttgctgaa ggctcaggct      60
tggaccagct ttagtc                                                      76

<210> SEQ ID NO 9
```

```
<211> LENGTH: 105
<212> TYPE: DNA
<213> ORGANISM: Artificial
<220> FEATURE:
<223> OTHER INFORMATION: JS1

<400> SEQUENCE: 9
gattagcttg acccgctctg tagggtcgcg actacgtgag ctagggctcc ggactgggct      60
gtatagtcga gtctgatctc gccccgacaa ctgcaaaccc caact                    105
```